United States Patent [19]

Anisovich et al.

[11] 4,417,355

[45] Nov. 22, 1983

[54] X-RAY FLUORESCENCE SPECTROMETER

[75] Inventors: Kliment V. Anisovich; Nikolai I. Komyak; Zaurbek K. Menbaev, all of Leningrad, U.S.S.R.

[73] Assignee: Leningradskoe NPO "Burevestnik", Leningrad, U.S.S.R.

[21] Appl. No.: 223,268

[22] Filed: Jan. 8, 1981

[51] Int. Cl.³ .............................................. G01N 23/22
[52] U.S. Cl. ......................................... 378/49; 378/83
[58] Field of Search ....................... 378/49, 82, 83, 84

[56] References Cited

U.S. PATENT DOCUMENTS 3,042,801  7/1962  Holliday ................................. 378/49
3,105,902 10/1963  Ostrofsky .............................. 378/49
4,091,282  5/1978  Anisovich ............................. 378/49

Primary Examiner—Craig E. Church
Attorney, Agent, or Firm—Fleit, Jacobson, Cohn & Price

[57] ABSTRACT

An X-ray fluorescence spectrometer comprising an X-ray source, a sample holder spaced from the X-ray source at a distance which ensures the illumination of the central portion of the sample not less than 0.3 ZU erg./s.cm².w, where Z is the atomic weight of material of the X-ray anode and U is the voltage across the X-ray source, in kilovolts. The spectrometer further comprises a curved analyzing cristal for focusing the fluorescent radiation of the sample at an X-ray detector. The analyzing cristal and the detector are installed in an evacuated chamber. The X-ray source and the sample holder are positioned outside the evacuated chamber which has a window for passing X-ray radiation. The sample holder is positioned so that the average distance between the sample surface portion which produces radiation incident on the analyzing cristal and the window does not exceed the distance between said sample surface portion and the focus of the X-ray source.

2 Claims, 1 Drawing Figure

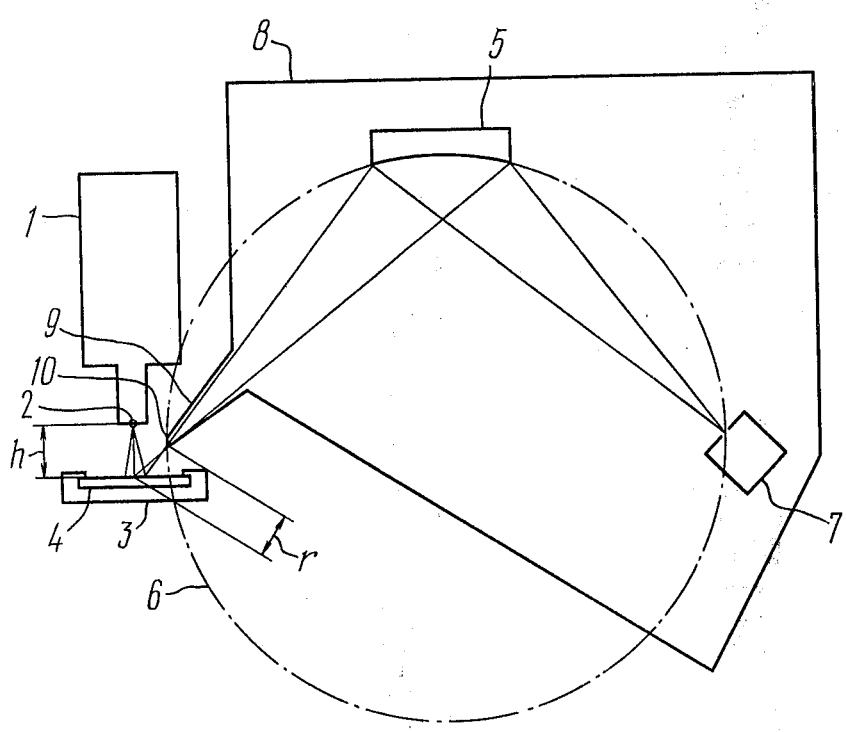

X-RAY FLUORESCENCE SPECTROMETER

FIELD OF THE INVENTION

The present invention relates to spectrometers, and more particularly to X-ray fluorescence spectrometers.

The present invention can be used for chemical analysis in metallurgy, geology, chemical industry, etc.

BACKGROUND OF THE INVENTION

In X-ray fluorescence spectrometers, the chemical composition of a substance is determined by irradiating the sample under test with X-rays and by recording the secondary X-ray fluorescent radiation emitted by the sample. Resolution of the sample fluorescence into its component wavelengths is achieved with the aid of an analyzing cristal which may be flat (as in Soller spectrometers) or curved (as in Johann or Johansson spectrometers). In the latter case the analyzing cristal provides focusing of the radiation reflected thereby at the focal circle defined by the curve of the planes of the analyzing cristal.

In the X-ray spectrometers commonly used nowadays the sample is positioned at a considerable distance (from 20 to 40 mm) from the focus of the X-ray source (X-ray tube). Therefore, to ensure the required sensitivity, such spectrometers must employ powerful big-sized X-ray tubes.

As is well known, soft X-ray radiation (having a relatively long wavelength) is strongly absorbed by air, which makes it impossible to determine the concentrations of light chemical elements in the test sample unless some special measures are taken to ensure a small degree of absorption of soft X-ray radiation.

In the known X-ray fluorescence spectrometers this is achieved by installing the whole X-ray system, including the X-ray source and the sample-loading device, in a chamber which is evacuated or filled with a light gas (helium). Such spectrometers make possible determination of concentrations of both heavy and light chemical elements.

However, spectrometers with such an evacuated chamber do not permit analysis of the samples susceptible to destruction by vacuum, such as solutions, powders, vegetable substances, etc. This substantially narrows the range of substances which can be analyzed. The employment of a helium-filled chamber makes the spectrometer very cumbersome in construction and use.

Besides, in such spectrometers the sample is difficult of access, which increases the time required for analysis and therefore reduces the productivity of the spectrometer and makes the sample-loading device more complicated.

Furthermore, breaking of vacuum occurring in such spectrometers when a sample is installed or removed necessitates restoration of vacuum each time a sample is installed. This also leads to increase in the time required by analysis and, besides, makes necessary the use of powerful vacuum pumps, which considerably increases the size and weight of the spectrometer.

Known in the art is an X-ray spectrometer wherein the X-ray source is positioned fairly close to the surface of the sample. Such a spectrometer comprises an X-ray source, a sample holder positioned across the radiation path of the X-ray source and spaced from the X-ray source at a distance which ensures the illumination of the central portion of the sample surface not less than $0.3\ ZU$ erg/s. $cm^2$.w, where X is the atomic weight of material of the X-ray anode and U is the voltage across the X-ray source, in kilovolts, a curved analyzing cristal for focusing the fluorescent radiation of the sample, the curve of the planes of the analyzing cristal defining a focal circle, and a detector for recording the radiation reflected by the analyzing cristal, the sample holder being positioned so that the distance between the focal circle and the sample surface exposed to radiation does not exceed the product of the distance between the focus of the X-ray source and said sample surface by the ratio between the diameter of the focal circle and the length of the analyzing cristal (cf. U.S. Pat. No. 4,091,282).

To provide the above-mentioned illumination of the sample surface, the X-ray source must be located very close to the sample. The distance between the focal circle and the sample in such a spectroueter is also small. Thanks to the small distance between the X-ray source and the sample, such a spectrometer provides considerable increase in the aperture ratio of the spectrometer and thus makes it possible to drastically (several tens of times) reduce the amount of power consumed by the X-ray tube, and hence its size and weight.

However, in the absence of an evacuated chamber, such a spectrometer is not capable of determining the concentrations of light chemical elements, e.g. having atomic weight below 22, because of strong absorption of soft X-ray radiation by air.

SUMMARY OF THE INVENTION

Accordingly, it is an object of the present invention to provide an X-ray fluorescence spectrometer which is capable of determining the concentrations of light chemical elements in samples susceptible to destruction by vacuum.

Another object of the present invention is to provide an X-ray fluorescence spectrometer which permits quick determination of the concentrations of light chemical elements in the test sample.

Still another object of the present invention is to provide an X-ray fluorescence spectrometer capable of determining the concentrations of light chemical elements in the test sample and having a small size and weight.

Still another object of the present invention is to provide an X-ray fluorescence spectrometer which permits determination of the concentrations of light chemical elements in the test sample without making the sample difficult of access.

Still another object of the present invention is to provide an X-ray fluorescence spectrometer which permits determination of the concentrations of light chemical elements in the test sample without necessitating restoration of vacuum each time a sample is installed.

With these and other objects in view there is proposed an X-ray fluorescence spectrometer comprising an X-ray source, a sample holder positioned across the radiation path of the X-ray source and spaced from the X-ray source at a distance which ensures the illumination of the central portion of the sample surface not less than $0.3\ ZU$ erg/s.$cm^2$.w, where Z is the atomic weight of material of the X-ray anode and U is the voltage across the X-ray source, in kilovolts, a curved analyzing cristal for focusing the fluorescent radiation of the sample, the curve of the planes of the analyzing cristal defining a focal circle, and a detector for recording the radiation reflected by the analyzing cristal, wherein, according to the invention, the detector and the analyzing cristal are installed in an evacuated chamber, the X-ray source and the sample holder being positioned outside the evacuated chamber which is provided with a window positioned on the focal circle across the path of the fluorescent radiation of the sample, the sample holder being positioned so that the average distance between the sample surface portion which produces fluorescent radiation incident on the analyzing cristal and the window does not exceed the distance between this sample surface and the focus of the X-ray source.

The proposed spectrometer allows for determining the concentrations of light chemical elements in the test sample because, with the distances between the sample and the chamber window and between the X-ray source and the sample chosen as described above, these distances are so small to create little absorption of soft X-ray radiation.

At the same time, the proposed spectrometer makes it possible to analyze a wide range of objects, including those susceptible to destruction by vacuum, provides an easy access to the test sample and eliminates the need for restoring vacuum each time a sample is installed, thanks to the arrangement of the sample holder and the X-ray source outside the evacuated chamber. Such an arrangement of the sample holder and the X-ray source can be easily accomplished inspite of the small distances between the sample and the source because the required sensitivity of the spectrometer is ensured in this case by using a small-power X-ray source having a small size. Thanks to the easy access to the sample and elimination of the need for restoring vacuum each time a sample is installed, the spectrometer is capable of performing a rapid analysis and has a small size and weight.

Preferably, the window of the evacuated chamber is positioned at the top of a prism-shaped projection of the chamber, the projection of the protruding portion on the plane of the focal circle being bounded by two line segments converging at the focal circle at an angle to each other equal to the aperture angle of the analyzing cristal.

The aforementioned and other objects and advantages of the present invention will become more apparent upon consideration of the following detailed description of its preferred embodiment taken in conjunction with the accompanying drawing.

BRIEF DESCRIPTION OF THE DRAWING

The drawing shows the arrangement of the elements of an X-ray fluorescence spectrometer constructed according to the present invention.

DETAILED DESCRIPTION OF THE INVENTION

Referring to the drawing, the X-ray fluorescence spectrometer comprises an X-ray source which is an X-ray tube 1 with a focal spot 2, and a sample holder 3 arranged across the radiation path of the tube 1. In the drawing, the spectrometer is shown with a sample 4 which is a pellet placed in the holder 3. The spectrometer further comprises a curved focusing analyzing cristal 5 defining by the curve of its planes the location of a focal circle 6, and a detector 7 for recording radiation reflected by the analyzing cristal 5. The detector 7 may be, for example, a proportional gaseous discharge counter.

The analyzing cristal 5 and the detector 7 are installed in an evacuated chamber 8. The X-ray tube I and the sample holder 3 with the sample 4 are positioned outside the chamber 8.

The chamber 8 has a protruding portion 9 shaped and positioned so that its projection on the plane of the focal circle 6 is bounded by two line segments converging at the focal circle 6 at an angle to each other equal to the aperture angle of the analyzing cristal 5. The chamber 8 is provided with a window 10 for passing X-ray radiation. The window 10 is positioned at the top of the prism-shaped projection 9 across the path of fluorescent radiation emitted by the simple 4, the analyzing cristal 5 being positioned across the path of fluorescent radiation passing through the window 10. The window 10 is made of material permitting passage of X-ray radiation, such as polypropylene.

The sample holder 3 is spaced from the X-ray tube I at a distance which ensures the illumination of the central portion of the sample surface not less than 0.3 ZU erg/s.cm$^2$.w, where Z is the atomic weight of material of the X-ray anode and U is the voltage across the tube I, in kilovolts. The sample holder 3 is so positioned in relation to the window 10 that the average distance "r" between the sample surface portion which produces radiation incident on the analyzing cristal 5 and the window 10 does not exceed the distance "h" between this sample surface portion and the focal spot 2.

The spectrometer operates as follows.

The primary radiation of the X-ray tube I coming from the focal spot 2 illuminates the sample 4 wherein a secondary X-ray fluorescent radiation is induced. The fluorescent radiation of the sample 4 passes through the window 10 into the evacuated chamber 8, is reflected from the analyzing cristal 5, focused on the detector 7 and recorded by the latter.

With the illumination of the central portion of the sample surface not less than 0.3 ZU erg/s.cm$^2$.w, the distance "h" between the focal spot 2 of the X-ray tube I and the sample surface will be small enough to create a relatively small weakening of the X-ray radiation leaving the tube I. This ensures a sufficiently effective excitation of light chemical elements present in the sample 4. Since the average distance "r" between the sample surface portion which produces radiation incident on the analyzing cristal 5 and the window 10 does not exceed the distance "h", the distance "r" will be small enough to create, in the path between the sample 4 and the window 10, a relatively small weakening of the soft X-ray fluorescent radiation of the light chemical elements effective excitation of which is ensured at the chosen value of the distance "h". Thereupon, when the X-ray fluorescent radiation passes through the evacuated chamber 8, this radiation practically does not weaken. Therefore the intensity of the soft radiation produced by light chemical elements present in the sample 4 will be enough to allow determination of the concentrations of said elements in the sample 4.

The arrangement of the window 10 at the top of the prism-shaped projection 9 shaped and positioned as described above allows the window 10 to be brought as near to the sample 4 as possible, without causing any losses in the fluorescent radiation passing inside the portion 9, and thus provides the maximum reduction in the absorption of the fluorescent radiation of the sample 4 in the path between the sample 4 and the window 10. The positioning of the window 10 on the focal circle 6 provides the maximum reduction in the area of the window 10, and hence in the thickness of its material and in its ability to absorb the fluorescent radiation of the sample 4.

According to this disclosure, the function of the dispersing element is performed by an analyzing cristal. Of course, this does not imply that the latter cannot be replaced by a technical equivalent, for example, a focusing diffraction grating.

An X-ray fluorescence spectrometer has been built according to the arrangement shown in the drawing. This spectrometer employs an acute-focus 5-watt 25-kilovolt X-ray tube having a silver anode, a Johansson analyzing cristal made of RbAP and having dimensions of 20×40 mm, and an argon proportional counter, with the distances "r" and "h" being 3 mm and the diameter of the focal circle being 150 mm. Such a spectrometer is capable of determining the concentrations of chemical elements having atomic weight from II (sodium) to 92 (titanium). The spectrometer has a small weight (about 15 kg) and size (about 400×400×150 mm).

While the invention is described herein in the terms of the preferred embodiments, numerous modifications may be made without departure from the spirit and scope of the invention as defined in the appended claims.

We claim:

1. An X-ray fluorescence spectrometer comprising:
an evacuated chamber having a window for passing X-ray radiation;
an X-ray source positioned outside said evacuated chamber;
a sample holder for accomodating a sample to be investigated, said sample holder being positioned outside said evacuated chamber across the radiation path of said X-ray source and spaced from said X-ray source at a distance which ensures the illumination of the central portion of the surface of said sample not less than 0.3 ZU erg/s.cm$^2$.w, where Z is the atomic weight of material of the anode of said X-ray source and U is the voltage across said X-ray source, in kilovolts;
a curved analyzing crystal installed in said evacuated chamber for focusing the X-ray fluorescent radiation of said sample and defining by the curve of its planes a focal circle, said window of said evacuated chamber being positioned on said focal circle across the path of the X-ray fluorescent radiation of said sample, the average distance between the sample surface portion which produces fluorescent radiation incident on said analyzing crystal and said window not exceeding the distance between said sample surface portion and the focus of said X-ray source, and
a detector installed in said evacuated chamber for recording the X-ray fluorescent radiation of said sample focused by said analyzing crystal, wherein said evacuated chamber has a prism-shaped projection which on the plane of said focal circle is bounded by two line segments converging at said focal circle at an angle to each other equal to the aperture angle of said analyzing crystal, said window of said evacuated chamber being positioned at the top of said prism-shaped projection.

2. An X-ray fluorescence spectrometer comprising:
an evacuated chamber;
an X-ray source;
a sample holder positioned across the radiation path of said source, said sample holder positioned at such a distance from the focus of said X-ray source that the specific illumination in the central region of the surface of a sample is not less than 0.3 ZU erg/s.cm$^2$.w, where Z is the atomic weight of the material of the anode of said X-ray source, and U is the voltage across said X-ray source in kilovolts;
a curved analyzing crystal, the curvature of the planes of said crystal determining the diameter of a focus circle, said analyzing crystal focusing the fluorescent radiation of the sample arranged in said sample holder;
an X-ray detector for recording the radiation focused by said analyzing crystal;
said analyzing crystal and said detector being positioned in said evacuated chamber of the spectrometer and said X-ray source and said sample holder being positioned in the open air outside said evacuated chamber;
said evacuated chamber having a vacuum sealed inlet window transparent to X-rays, said window forming an inlet slot of said spectrometer, said inlet slot being positioned across the beam of fluorescent X-rays of said sample and arranged at said focus circle;
said sample holder being positioned with respect to said inlet slot in such manner that the average distance between the region on the surface of the sample being analyzed and said inlet slot does not exceed the distance from that region of the sample to the focus of said X-ray source.

* * * * *